United States Patent
Marks

(10) Patent No.: US 9,809,849 B2
(45) Date of Patent: Nov. 7, 2017

(54) METHODS AND SYSTEMS FOR PURE DYE INSTRUMENT NORMALIZATION

(71) Applicant: LIFE TECHNOLOGIES CORPORATION, Carlsbad, CA (US)

(72) Inventor: Jeffrey Marks, Mountain View, CA (US)

(73) Assignee: Life Technologies Corporation, Carlsbad, CA (US)

(*) Notice: Subject to any disclaimer, the term of this patent is extended or adjusted under 35 U.S.C. 154(b) by 0 days.

(21) Appl. No.: 15/016,713

(22) Filed: Feb. 5, 2016

(65) Prior Publication Data

US 2016/0237474 A1 Aug. 18, 2016

Related U.S. Application Data

(60) Provisional application No. 62/112,964, filed on Feb. 6, 2015.

(51) Int. Cl.
  *G01N 21/64* (2006.01)
  *C12Q 1/68* (2006.01)
  *G01N 21/27* (2006.01)

(52) U.S. Cl.
  CPC .......... *C12Q 1/686* (2013.01); *G01N 21/274* (2013.01); *G01N 21/6452* (2013.01); *G01N 21/6428* (2013.01); *G01N 2021/6421* (2013.01); *G01N 2201/04* (2013.01); *G01N 2201/068* (2013.01); *G01N 2201/12746* (2013.01)

(58) Field of Classification Search
  CPC ...... Y10T 436/10; G01N 31/00; G01N 33/00; G01N 21/6428; G01N 2201/12746; G01J 1/58
  See application file for complete search history.

(56) References Cited

U.S. PATENT DOCUMENTS

| 7,630,849 B2 | 12/2009 | DeSimas et al. |
| 7,662,750 B2 | 2/2010 | Bahatt et al. |
| 8,084,260 B2 * | 12/2011 | Gunstream .......... G01N 21/278 422/63 |

(Continued)

FOREIGN PATENT DOCUMENTS

| EP | 1677097 A1 | 5/2006 |
| WO | 2008003053 A2 | 1/2008 |

*Primary Examiner* — Marcus Taningco
(74) *Attorney, Agent, or Firm* — Mauriel Kapouytian Woods LLP; Michael Mauriel

(57) ABSTRACT

The present teachings relate to a method and system for normalizing spectra across multiple instruments. In an embodiment of the present invention, the method comprises at least one reference instrument and a test instrument. Each instrument comprises at least one excitation filter and at least one emission filter arranged in pairs. Each instrument further comprises a pure dye plate comprising a plurality of wells. Each well contains a plurality of dyes where each dye comprises a fluorescent component. Fluorescent spectra are obtained from each instrument for each dye across multiple filter combinations to contribute to a pure dye matrix Mref for the reference instrument and pure dye matrix M for the test instrument. The pure dye spectra can then be multiplied by correction factors for each filter pair to result in corrected pure dye spectra, then normalized and the multicomponenting data can be extracted.

16 Claims, 8 Drawing Sheets

(56) References Cited

U.S. PATENT DOCUMENTS

| | | | | |
|---|---|---|---|---|
| 8,285,492 B2* | 10/2012 | Gunstream | .......... | C12Q 1/6851 |
| | | | | 702/30 |
| 9,291,564 B2* | 3/2016 | Xu | ................ | G01N 21/276 |
| 2007/0100569 A1* | 5/2007 | DeSimas | ................ | G01N 31/00 |
| | | | | 702/85 |
| 2008/0001099 A1* | 1/2008 | Sharaf | ................ | G01N 21/274 |
| | | | | 250/459.1 |
| 2008/0178653 A1 | 7/2008 | Gunstream | | |

* cited by examiner

| DyeMixtures |
|---|
| ABY/MP |
| Cy5/ROX |
| FAM/MP |
| FAM/ROX |
| JUN/MP |
| NED/ROX |
| VIC/MP |
| VIC/ROX |

FIG. 4A

| Dyes | Main Channel |
|---|---|
| FAM | X1M1 |
| SYBR | X1M1 |
| VIC | X2M2 |
| HEX | X2M2 |
| NED | X3M3 |
| ABY | X3M3 |
| ROX | X4M4 |
| JUN | X4M4 |
| CY5 | X5M5 |
| MP | X5M5 |

FIG. 4B

METHODS AND SYSTEMS FOR PURE DYE INSTRUMENT NORMALIZATION

CROSS-REFERENCE TO RELATED APPLICATIONS

This application claims the benefit of priority of U.S. provisional application Ser. No. 62/112,964, filed Feb. 6, 2015, which is incorporated herein by reference in its entirety.

BACKGROUND

Currently, genomic analysis, including that of the estimated 30,000 human genes is a major focus of basic and applied biochemical and pharmaceutical research. Such analysis may aid in developing diagnostics, medicines, and therapies for a wide variety of disorders. However, the complexity of the human genome and the interrelated functions of genes often make this task difficult. One difficulty commonly faced is the inability of researchers to easily compare results of experiments run on multiple instruments. Physical variations in the parameters of components such as light sources, optical elements and fluorescence detectors, for example, can result in variation in the results of analyses on what may be identical biological samples. There is, therefore, a continuing need for methods and apparatus to aid in minimizing the variations in the components. One such methodology is described in the present teachings.

DRAWINGS

One skilled in the art will understand that the drawings, described herein, are for illustration purposes only. The drawings are not intended to limit the scope of the present teachings in any way.

FIG. 4A illustrates dye mixtures used in various embodiments of the present teachings.

FIG. 4B illustrates pure dyes and main channel filter combinations for various embodiments of the present teachings.

SUMMARY OF THE INVENTION

Figure 1:
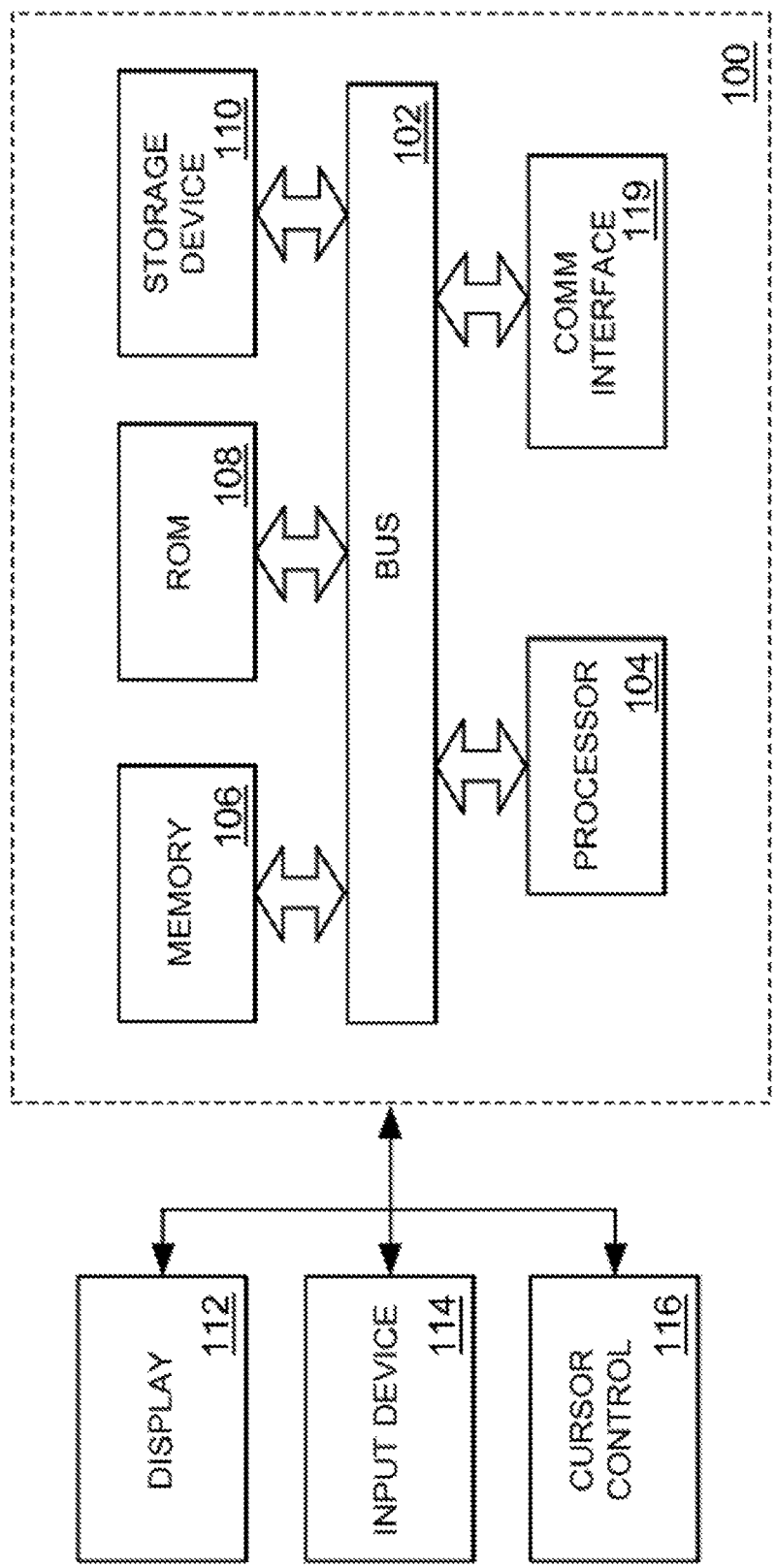
FIG. 1 illustrates a computer system on which embodiments of the present teachings can be implemented.

The present teachings relate to a method and system for normalizing spectra across multiple instruments. In an embodiment of the present invention, the method comprises at least one reference instrument and a test instrument. Each instrument comprises at least one excitation filter and at least one emission filter arranged in pairs. Each instrument further comprises a pure dye plate comprising a plurality of wells. Each well contains a plurality of dyes where each dye comprises a fluorescent component. Fluorescent spectra are obtained from each instrument for each dye across multiple filter combinations to contribute to a pure dye matrix Mref for the reference instrument and pure dye matrix M for the test instrument. The pure dye spectra can then be multiplied by correction factors for each filter pair to result in corrected pure dye spectra, then normalized and the multicomponenting data can be extracted.

In another embodiment, the fluorescent spectra from the reference instrument and the test instrument are first normalized and then averaged over multiple wells to form the pure dye matrices.

In another embodiment, dye matrix M is multiplied by a set of adjustment factors that are iteratively modified to minimize the difference between matrix M and matrix Mref.

In another embodiment, the adjustment factors are modified between 0 and 1

In another embodiment, the correction factor is the product of the emission filter factor and the excitation filter factor.

In another embodiment, the corrected pure dye spectra are normalized to a value of one.

In another embodiment, the multicomponent data is derived from the product of the fluorescence data and the pseudo-inverse dye matrix M.

According to various embodiments, a system for normalizing laboratory instruments with pure dyes is presented. The system can comprise a pure dye reference matrix Mref. The system can further comprise a test instrument. The test instrument can comprise a plurality of filter pairs and at least one pure dye plate. The system can further comprise a computer system in communication with the test instrument and comprising at least one processor and at least one computer-readable medium comprising instructions for pure dye normalization executable by the processor.

In another embodiment, the filter pairs comprise an excitation filter and an emission filter.

In another embodiment, the pure dye plate comprises at least one fluorescent pure dye contained in a sample plate comprising a plurality of sample wells.

In another embodiment, the processor executes instructions designed to generate a test spectra matrix M.

In another embodiment, matrix Mref and matrix M comprise normalized and averaged spectra.

In another embodiment, the processor further executes instructions designed to iteratively adjust matrix M until the difference between matrix M and matrix Mref is minimized.

In another embodiment, the processor further executes instructions designed to modify matrix M based on correction factors for each filter pair.

DESCRIPTION OF VARIOUS EMBODIMENTS

The following description of various embodiments is merely exemplary in nature and is in no way intended to limit the present teachings, applications or uses. Although the present teachings will be discussed in some embodiments as relating to polynucleotide amplification, such as polymerase chain reaction (PCR), such discussion should not be regarded as limiting the present teaching to only those applications.

FIG. 1 is a block diagram that illustrates a computer system 100 upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102, and instructions to be executed by processor 104. Memory 106 also may be used for storing temporary variables or other intermediate information during execution of instructions, corresponding to the methods and present teachings, to be executed by processor 104. Computer system 100 further includes a read only memory (ROM) 108 or other static storage device coupled to bus 102 for storing static information and instructions for processor 104. A storage device 110, such as, for example, but not limited to a solid-state disk, a magnetic disk or optical disk, is provided and coupled to bus 102 for storing information and instructions.

Computer system 100 may be coupled via bus 102 to a display 112, such as, for example, but not limited to a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as, for example, but not limited to a mouse, a trackball or cursor direction keys for communicating direction information and command selections to processor 104 and for controlling cursor movement on display 112. This input device typically has two degrees of freedom in two axes, a first axis (e.g., x) and a second axis (e.g., y), that allows the device to specify positions in a plane.

Consistent with certain embodiments of the present teachings, setup and calibration of laboratory instruments can be performed by computer system 100 in response to processor 104 executing one or more sequences of one or more instructions contained in memory 106. Such instructions may be read into memory 106 from another computer-readable medium, such as, for example storage device 110. Execution of the sequences of instructions contained in memory 106 causes processor 104 to perform the process states described herein. Alternatively hard-wired circuitry may be used in place of, or in combination with, software instructions to implement the present teachings. Thus, implementations of the present teachings are not limited to any specific combination of hardware circuitry and software.

The term "computer-readable medium" as used herein refers to any media that participates in providing instructions to processor 104 for execution. Such a medium may take many forms, including but not limited to, nonvolatile media, volatile media, and transmission media. Nonvolatile media can include but not be limited to, for example, optical or magnetic disks, such as storage device 110. Volatile media can include but not be limited to dynamic memory, such as memory 106. Transmission media can include but not be limited to coaxial cables, copper wire, and fiber optics, including the wires that comprise bus 102. Transmission media can also take the form of acoustic or light waves, such as those generated during radio-wave and infrared data communications.

Common forms of computer-readable media can include, for example, but not be limited to a floppy disk, flexible disk, hard disk, magnetic tape, or any other magnetic medium, a CDROM, any other optical medium, punch cards, paper tape, any other physical medium with patterns of holes, a RAM, PROM, EPROM, FLASH-EPROM, USB drive, jump drive or any other memory chip or cartridge, a carrier wave, or any other medium from which a computer can read.

Various forms of computer readable media may be involved in carrying one or more sequences of one or more instructions to processor 104 for execution. For example, the instructions may initially be carried on magnetic disk of a remote computer. The remote computer can load the instructions into its dynamic memory and send the instructions over, for example, a telephone line using a modem or wireless network. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

The present teachings are described with reference to Real-Time Polymerase Chain Reaction (RT-PCR) instruments. In particular, an embodiment of the present teachings is implemented for RT-PCR instruments employing optical imaging of well plates. Such instruments can be capable of simultaneously or sequentially measuring signals from a plurality of samples or spots for analytical purposes and often require calibration, including but not limited to processes involving: identifying ROI (Regions of Interest), determining background signal, uniformity and pure dye spectral calibration for multicomponent analysis. Calibration may also involve a RT-PCR verification reaction using a known sample plate with an expected outcome. One skilled in the art will appreciate that while the present teachings have been described with examples pertaining to RT-PCR instruments, their principles are widely applicable to other forms of laboratory instrumentation that may require calibration and verification in order to ensure accuracy and/or optimality of results.

The present teachings can be applied to RT-PCR instrument systems. Such RT-PCR instruments are well known to one skilled in the art. For example the present teachings can be applied to instruments such as, for example, but not limited to the Applied Biosystems Sequence Detection Systems 7500/7900/ViiA7 and Quant Studio systems, the Roche Applied Science LightCycler® 2.0 PCR amplification and detection system, the Bio-Rad MyiQ Single-Color Real-Time PCR Detection System, or the Stratagene Mx3000P™ Real-Time PCR System. Such instruments generally use some form of imaging system. While the present teachings are discussed relative to a CCD (charge-coupled detector) imaging system, the present teachings can be easily adapted to any form of imaging system.

In a system with a CCD imaging system, a CCD camera images a sample plate (typically a 96-well plate, although plates with other numbers of wells can be used or sample blocks containing individual tubes can also be used) at various selected dye fluorescent emission wavelengths during a PCR run. In such instruments, the wells are generally illuminated by an excitation light at wavelengths appropriate to each dye. In order to use the RT-PCR system to accurately monitor PCR amplification using the well emission intensities, the system must be calibrated for each dye emission.

Figure 2:
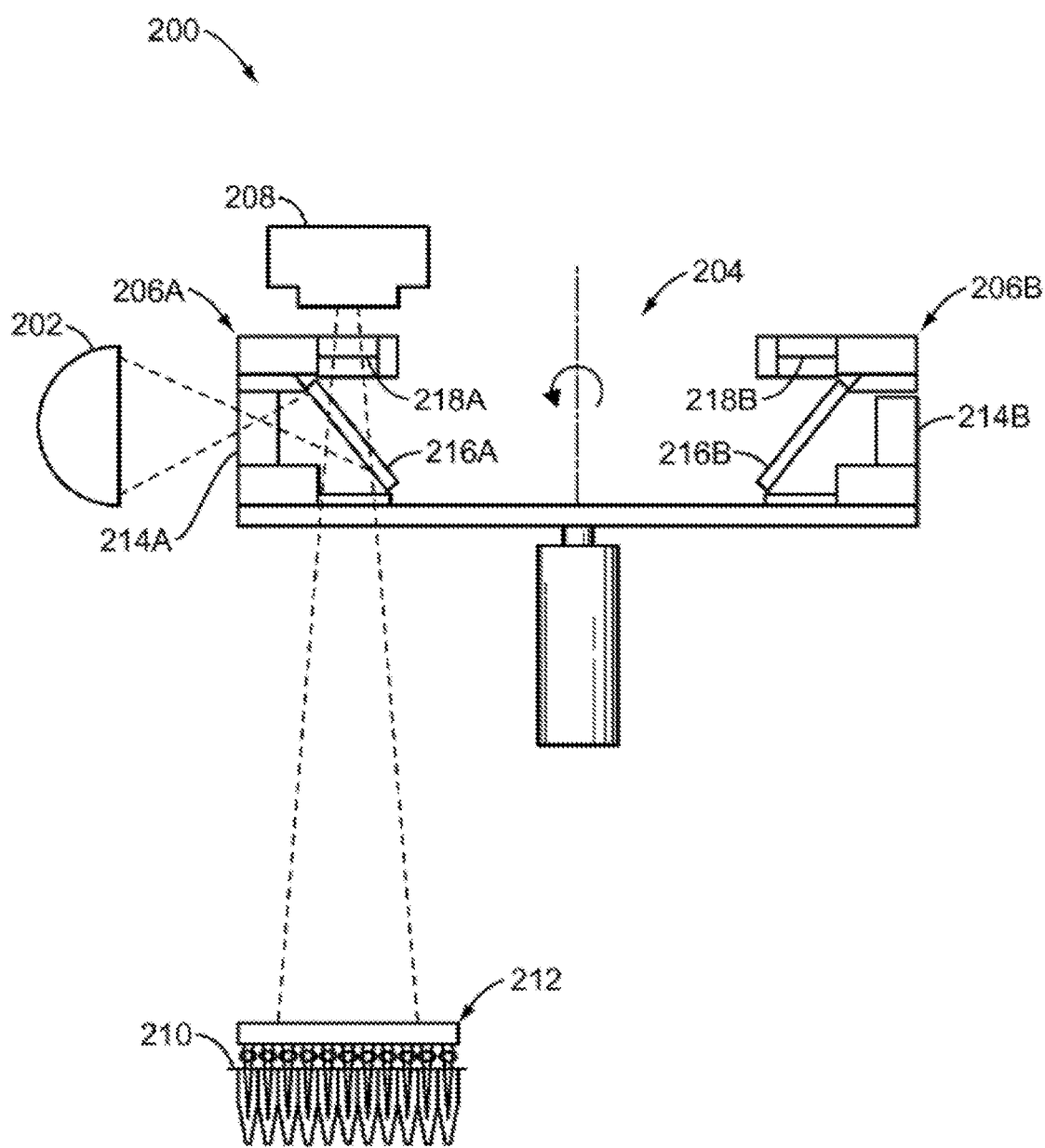
FIG. 2 illustrates a laboratory instrument upon which embodiments of the present teachings can be implemented.

FIG. 2 is a schematic illustration of a system used for fluorescent signal detection in accordance with implementations of the present invention. Detection system 200 is one example of a spectral detection system which can be used for RT-PCR data collection and processing in conjunction with aspects of the present invention. As illustrated, detection system 200 includes an excitation light source 202, at least one filter turret depicted by turret 204, a detector 208, a microwell tray 210 and well optics 212. Turret 204 can comprise multiple excitation filters or multiple emission filters or multiple excitation and emission filters paired for a specific dye. As illustrated, turret 204 includes filter cubes 206. A first filter cube 206A can include an excitation filter 214A, a beam splitter 216A and an emission filter 218A corresponding to one spectral species selected from a set of spectrally distinguishable species to be detected. A second filter cube 206B can include an excitation filter 214B, a beam splitter 216B and an emission filter 218B corresponding to a different spectral species selected from the set of spectrally distinguishable species to be detected.

Excitation light source 202 can be, for example, but not limited to a laser, broad spectrum light source, an LED or other type of excitation source capable of emitting a spectrum that interacts with spectral species to be detected by system 200. In this illustrated example, light source 202 emits a broad spectrum of light filtered by either excitation filter 214A or excitation filter 214B that passes through beam splitter 216A or beam splitter 216B and onto microwell tray 210 containing one or more spectral species.

Light emitted from light source 202 can be filtered through excitation filter 214A, excitation filter 214B or other filters that correspond closely to the one or more spectral species. The present teachings can be used with a plurality of spectrally distinguishable dyes such as, for example, but not limited to one or more of FAM, SYBR Green, VIC, JOE, TAMRA, NED CY-3, Texas Red, CY-5, Mustang Purple, ROX (passive reference) or any other fluorochromes that emit a signal capable of being detected. The target spectral species for the selected excitation filter provides the largest signal response while other spectral species with lower signal strength in the band-pass region of the filter contribute less signal response. Because the multiple fluorochromes may have this overlapping excitation and emission spectra, it is useful to apply a pure-dye matrix to correct for the small amount of "cross-talk" (signal from one dye detected with more than one filter set). This process is often referred to as multicomponenting.

In RT-PCR, amplification curves are often determined by normalizing the signal of a reporter dye to a passive reference dye in the same solution. Examples of reporter dyes can include, but not be limited to FAM, SYBR Green, VIC, JOE, TAMRA, NED CY-3, Texas Red, CY-5. An example of a passive reference can be, for example, but not limited to ROX. This normalization can be reported as normalized fluorescence values labeled as "Rn". Passive reference normalization enables consistent Rn values even if the overall signal level is affected by liquid volume, or overall illumination intensity. Passive reference normalization, however, cannot work properly if the ratio in signal between the reporter dye and reference dye varies, such as from instrument-to-instrument differences in the spectrum of the illumination. In order to adjust for these differences, normalization solutions can be manufactured to normalize the ratio of reporter to passive reference. An example of such a normalization solution can be a 50:50 mixture of FAM and ROX, which can be referred to as a "FAM/ROX" normalization solution.

This current method of instrument normalization, including reading fluorescence from the dye mixture to get a "normalization factor" to adjust Rn values requires additional expense. Typically, it can require the manufacture of normalization solutions and normalization plates, and additional time to run the additional calibrations. Further, this method only works for the dye mixtures you are calibrating with a standard paired filter set. A paired filter set can be a combination of an excitation filter and an emission filter. One skilled in the art will understand that the inclusion of an additional dye would require a different normalization solution and calibration process.

Manufacturing processes for producing the normalization solutions also contribute to variations in the response of the dyes. It has been found that it can be difficult to control dye concentrations due to the lack of an absolute fluorescence standard. In order to minimize these errors and variations it can be advantageous to target the dye ratio of the solution to within +/−15% of the desired mix, or within +/−10% of the desired mix from the manufacturing process. The manufacturing process is typically not controlled well enough to simply mix a 50:50 mixture of the dyes and meet those specifications, so an additional step in the process is necessary to adjust the dye mixture with a fluorimeter.

Acceptable percent variations disclosed above have been determined by studying the relationship between variation in dye mixture and Cts. A Ct is a common abbreviation for a "threshold cycle". RT-PCR, also known as Quantitative PCR or qPCR, can provide a method for determining the amount of a target sequence or a gene that is present in a sample. During PCR a biological sample can be, for example, subjected to a series of 35 to 40 temperature cycles. A cycle can have multiple temperatures. For each temperature cycle the amount of target sequence can theoretically double and is dependent on a number of factors not presented here. Since the target sequence contains a fluorescent dye, as the amount of target sequence increases i.e. amplified over the 35 to 40 temperature cycles the sample solution fluoresces brighter and brighter at the completion of each thermal cycle. The amount of fluorescence required to be measured by a fluorescence detector is frequently referred to as a "threshold", and the cycle number at which the fluorescence is detected is referred to as the "threshold cycle" or Ct. Therefore by knowing how efficient the amplification is and the Ct, the amount of target sequence in the original sample can be determined.

The tolerated percent variation described above can also be related to the standard deviation of Ct shifts in the instrument. It has been determined that a +/−15% variation in dye mixture can result in a standard deviation of 0.2 Cts which can be 2 standard deviations.

As presented above, the ability to reliably compare experimental results from multiple instruments is desirable and instrument-to-instrument variability is frequently an issue. This variability can result from two sources; variability of components within the instruments such as, for example, but not limited to lamps and filters as well as variability over time such as, for example lamp and filter aging. It would be advantageous to implement a process through which experimental results from multiple instruments can be reliably, easily and inexpensively compared. The teachings found herein disclose such a process.

The amount of fluorescent signal of a sample in an optical system can be dependent on several factors. Some of the factors can include, but not be limited to, the wavelength of the fluorescence light, the detector efficiency at that wavelength of fluorescence light, the efficiency of the emission filter, the efficiency of the excitation filter and the efficiency of the dye. The present teachings suggest that instrumentto-instrument variability can be minimized if the physical optical elements of the instruments could be normalized.

Figure 3:
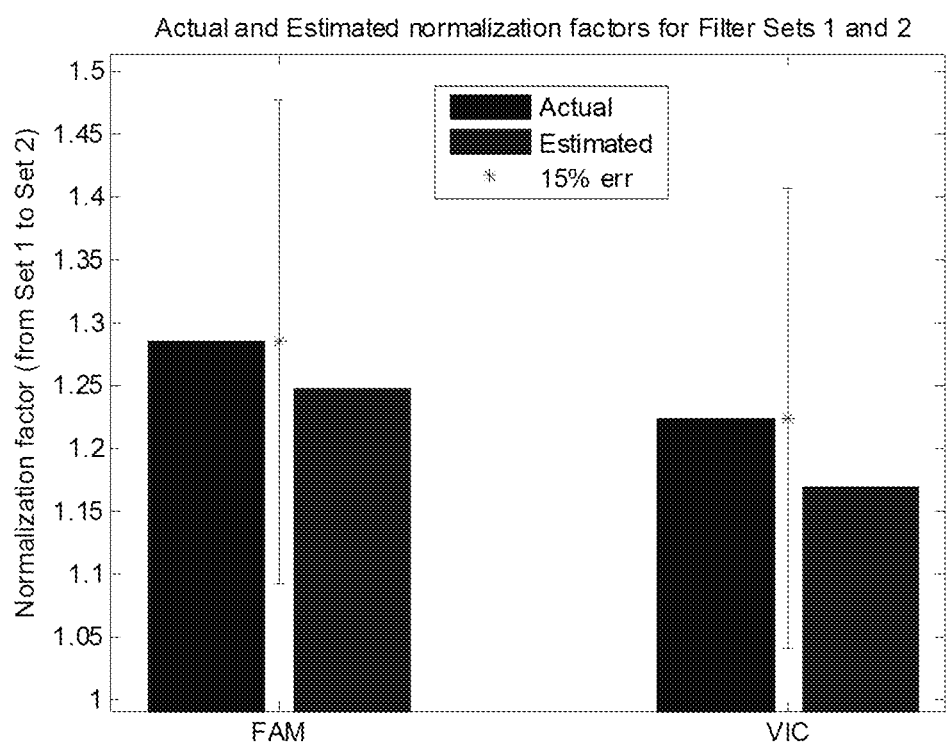
FIG. 3 illustrates actual and estimated normalization factors according to embodiments of the present teachings.

In one embodiment the normalization factors can be derived from pure dye spectra rather than from dye mixtures. Pure dyes can be easier to manufacture than dye mixtures, because the concentrations do not have to be exact, and there is only one fluorescent component. This concept was tested by normalizing two filter sets in an instrument using ten pure dyes and comparing the results to the normalization obtained from using dye mixtures. The normalization was implemented by determining a correction factor for each excitation filter and emission filter. The resulting correction factors can be used to normalize any combination of dyes, even from different instruments. FIG. 3 shows the results of such a comparison. The estimated normalization factors for the pure dyes are shown in red and the measured normalization factors from the mixed dye plates are shown in blue. One skilled in the art can see that the difference between the two sets of data are within the desired +/−15% variation presented previously.

In another embodiment, the normalization taught above was applied to multiple instruments of various types. Eight dye mixture solutions and ten pure dye solutions were created. Each solution was pipetted into eight wells of three 96 well plates. Potential spatial crosstalk was minimized by pipetting into every other well. The dye mixtures used are shown in FIG. 4A and the pure dyes used are shown in FIG. 4B. In addition, the instruments used included six sets of filters. FIG. 4B further identifies the filter pairs for the main optical channel for each pure dye. The excitation filter is depicted with an "X" and the emission filter is depicted with an "M".

Figure 5:
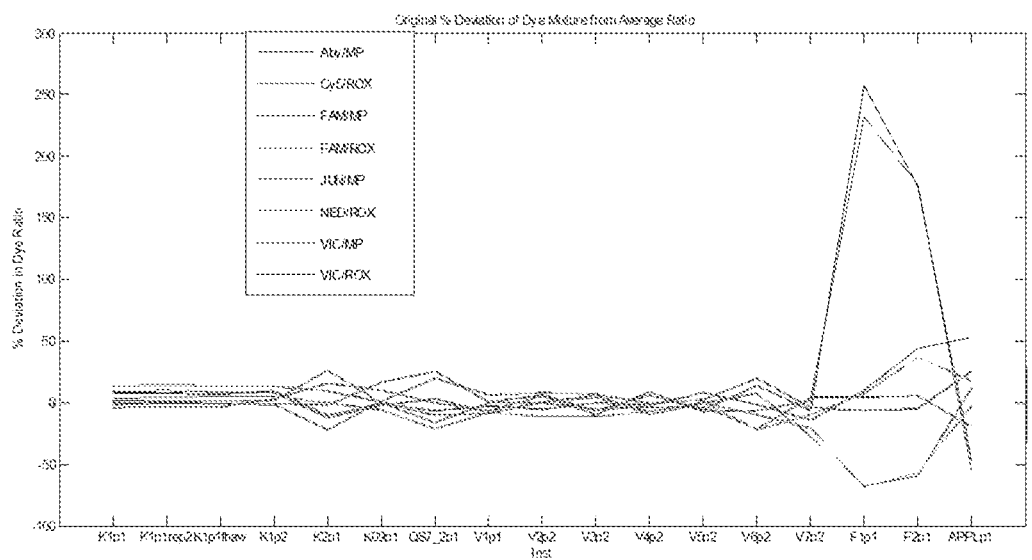
FIG. 5 illustrates percent deviation of dye mixtures before normalization according to various embodiments of the present teachings.

In an effort to quantify the effectiveness of the normalization process, the dye ratios were measured before and after normalization. FIG. 5 shows the percent deviation of dye mixtures from the average ratio for 17 tested instruments. The instruments are labeled on the X-axis and the percent deviation is on the Y-axis. One skilled in the art will notice that the deviation across the instruments is frequently greater than the desired +/−15% previously discussed. This data, therefore, shows a need for an improved normalization process such as the current teachings.

Figure 8:
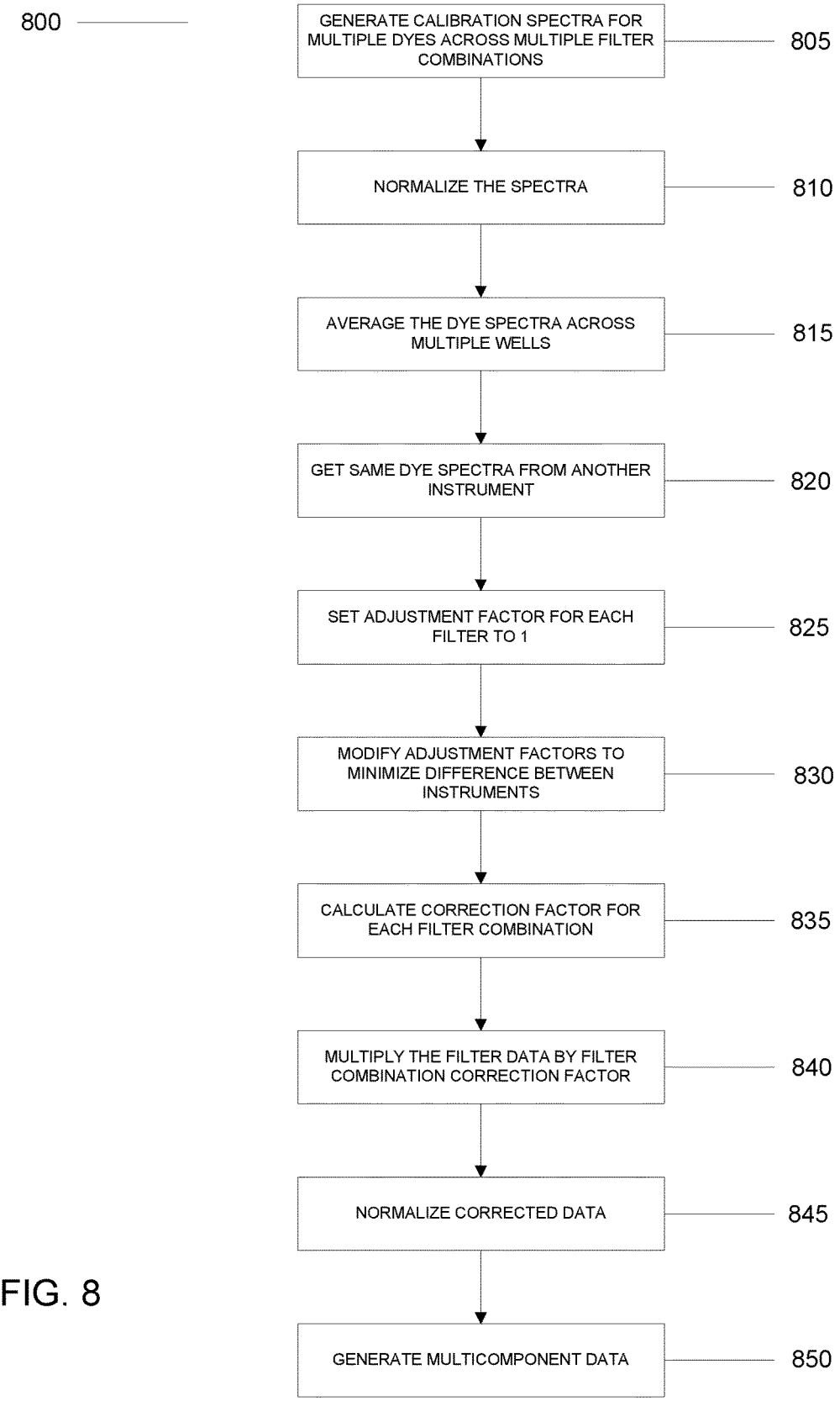
FIG. 8 is a flow chart depicting a normalization process according to various embodiments of the present teachings.

The current teachings were applied to all 17 instruments. The normalization method determines a correction factor for each individual filter rather than for each dye ratio. Because the instruments provided 6 excitation and 6 emission filters, 12 factors were determined. The process is shown in FIG. 8 and flowchart 800. In step 805, calibration spectra were generated for multiple dyes across multiple filter combinations. For the instruments being normalized, there were 10 pure dyes and 21 filter combinations. In step 810, the spectra were normalized so the maximum signal was 1. In step 815 the dye spectra are averaged across multiple wells. This averaging will result in producing one spectrum per dye. Collectively, the dye spectra can be referred to as a dye matrix "M" containing dye and filter combinations. At this point, a reference instrument is identified. The reference instrument could be an instrument or group of instruments that the test instruments will be normalized to. The same set of dye spectra used in the test instrument can be obtained from the reference instrument(s). In some embodiments the reference can be a group of instruments. In such an embodiment the spectra for each dye can be averaged across the group. This step is represented in flowchart 800 at step 820. As an example, the reference spectra can be referred to as matrix "Mref".

In step 825 each of the 12 filters has an adjustment factor initially set to 1. It can be desirable to multiply the adjustment factors times matrix "M" while iteratively modifying the adjustment factors between 0 and 1 and preferably between 0.04 and 1 until the difference between matrix "M" and matrix "Mref" is minimized as shown in step 830. In step 835, correction factors for each filter pair are calculated. The correction factor for each filter pair is the product of the emission filter factor times the excitation filter factor. The main channel filter pairs are shown in FIG. 4B. Once the correction factors for each filter pair has been determined, each filter pair factor can then be multiplied by the fluorescence data for the test instrument as well as for the pure dye spectra. The corrected pure dye spectra can then be renormalized to a maximum value of 1 as shown in step 845. The final step in the process at step 850 is to generate multicomponent data. One skilled in the art will understand the multicomponenting procedure to be the product of the fluorescence data and the pseudo-inverse of the dye matrix. The multicomponent values are already normalized so it will not be necessary to make dye specific corrections since the data has been normalized at the filter level.

Figure 6:
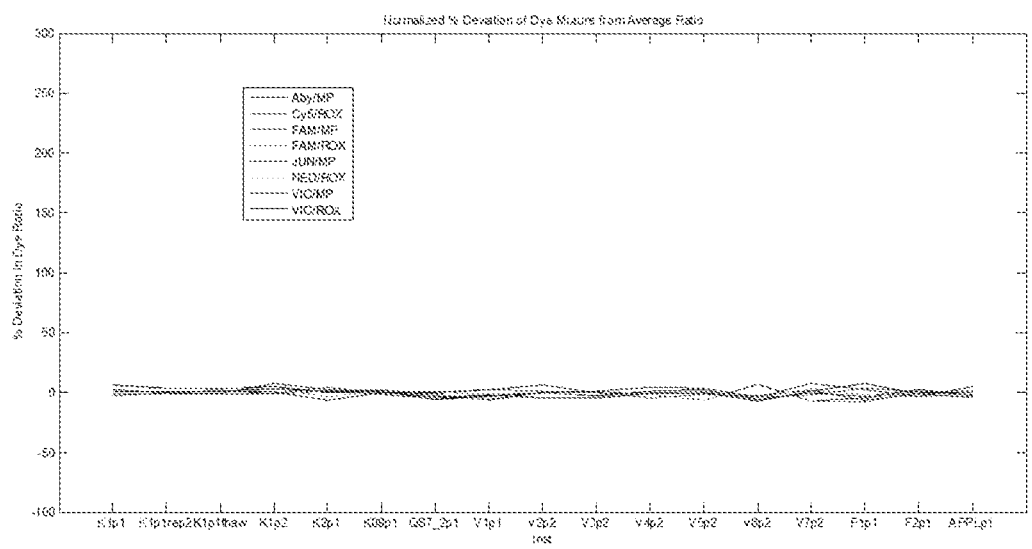
FIG. 6 illustrates percent deviation of dye mixtures after normalization according to various embodiments of the present teachings.
Figure 7:
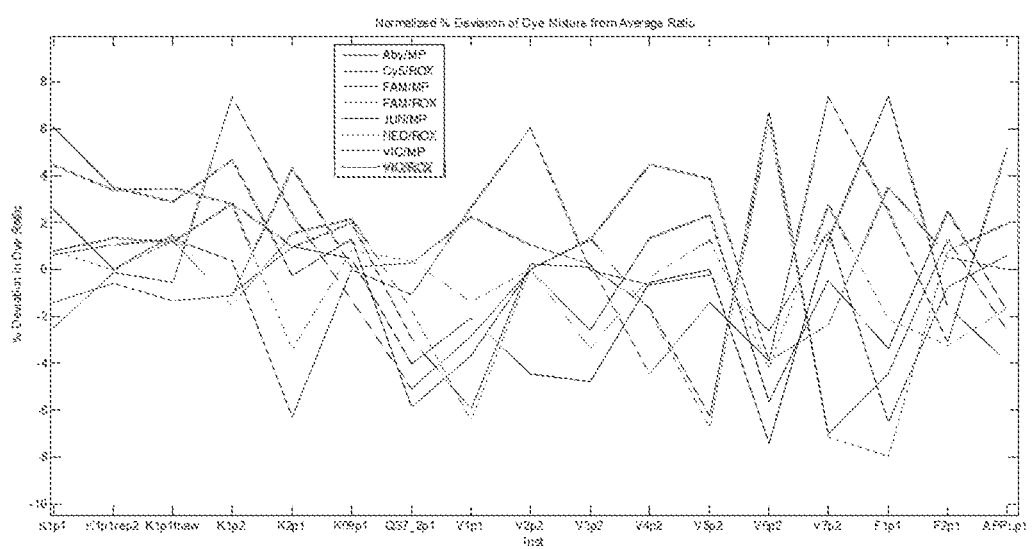
FIG. 7 illustrates a closer view of percent deviation of dye mixtures after normalization according to various embodiments of the present teachings.

At the completion of normalization the percent deviation of dye mixtures from the average ratio were calculated across all 17 instruments. The results are shown in FIG. 6. These results are significantly improved as compared to the data before normalization as shown in FIG. 5. A closer view of the normalized data from FIG. 6 is shown in FIG. 7, where the deviation after normalization has been reduced to +/−8% which is well below the target of +/−15% as presented previously.

Figure 9:
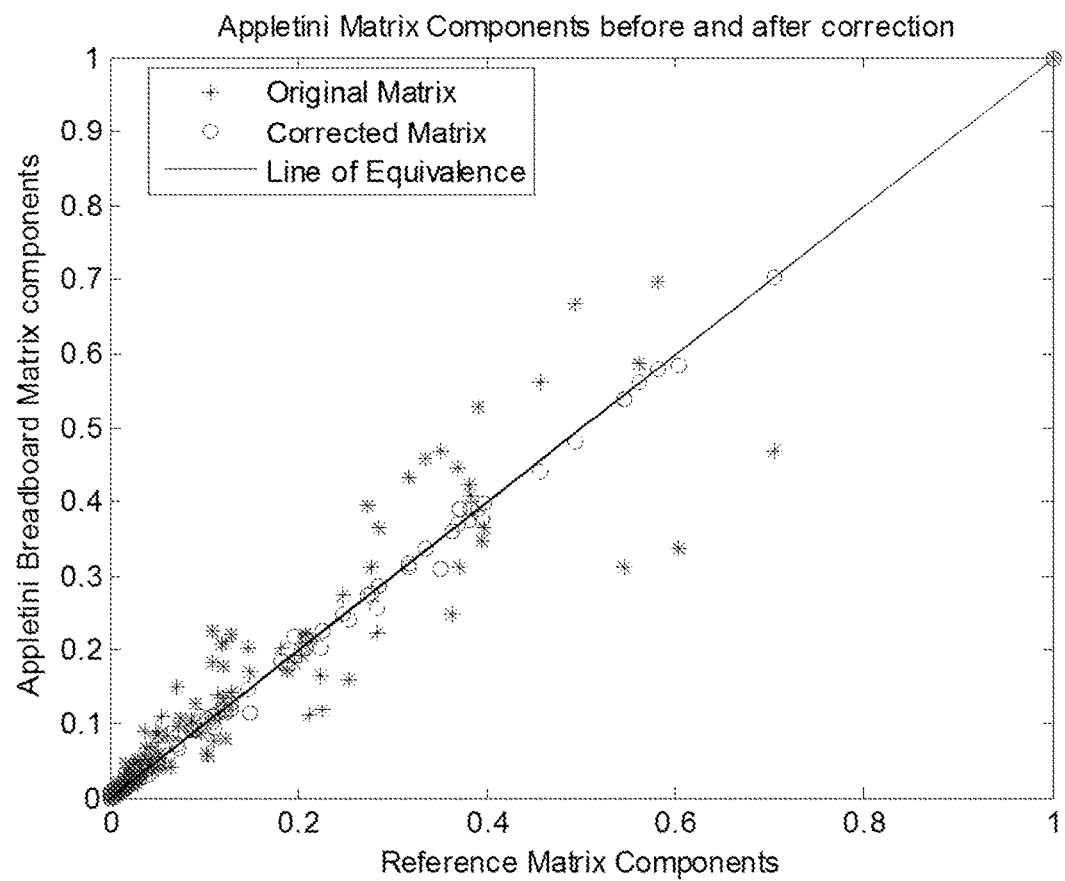
FIG. 9 illustrates the correlation between a test instrument and a reference instrument before and after normalization according to various embodiments of the present teachings.

FIG. 9 is a graph showing the comparison between original matrix "M" and corrected matrix "M" after normalization with reference matrix "Mref". The line of equivalence shows the data for both matrices are essentially the same and the normalization process is effective.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent.

It will be apparent to those skilled in the art that various modifications, variations and optimizations can be made to various embodiments described herein without departing from the spirit or scope of the present teachings. Thus, it is intended that the various embodiments described herein cover other modifications, variations and optimizations within the scope of the appended claims and their equivalents.

What is claimed:

1. A method for normalizing laboratory instruments with pure dyes, comprising:
    providing at least one reference instrument and a test instrument, each instrument comprising at least one excitation filter and at least one emission filter arranged in pairs;
    providing a plurality of pure dyes, each dye comprising a fluorescent component and contained in a pure dye plate comprising a plurality of wells;
    generating fluorescent spectra from the reference instrument and the test instrument for multiple pure dyes across multiple filter combinations;
    creating a pure dye matrix, Mref, for the reference instrument and a pure dye matrix, M, for the test instrument;
    calculating correction factors for each filter pair and multiplying the correction factors by the pure dye spectra;
    normalizing the corrected pure dye spectra;
    generating multicomponent data.

2. The method of claim 1, wherein the fluorescent spectra from the test and reference instruments are each normalized to a maximum of 1.

3. The method of claim 2, wherein each pure dye matrix comprises normalized spectra averaged over multiple wells.

4. The method of claim 1, wherein dye matrix M is multiplied by a set of adjustment factors and compared to dye matrix Mref.

5. The method of claim 4, wherein the adjustment factors are iteratively modified until the difference between matrix M and matrix Mref is minimized.

6. The method of claim 4, wherein the adjustment factors are iteratively modified between 0 and 1.

7. The method of claim 1, wherein the correction factor for each filter pair is the product of an emission filter factor and an excitation filter factor.

8. The method of claim 1, wherein the corrected pure dye spectra are normalized to a maximum of 1.

9. The method of claim 1, wherein the multicomponent data 1s the product of the fluorescence data and the pseudo-inverse of dye matrix M.

10. A system for normalizing laboratory instruments with pure dyes, the system comprising:
    a pure dye reference matrix, Mref;
    a plurality of instruments, each comprising:
        a plurality of filter pairs; and
        at least one pure dye plate;
    a computer system in communication with the plurality of instruments comprising:
        at least one processor; and
        at least one computer-readable medium comprising instructions for pure
    dye normalization executable by the processor to perform processing comprising: calculating correction factors for each filter pair; multiplying the correction factors by pure dye spectra; and
    normalizing the corrected pure dye spectra.

11. The system of claim 10, wherein the filter pairs each comprise an excitation filter and an emission filter.

12. The system of claim 10, wherein the pure dye plate comprises at least one fluorescent pure dye contained in a sample plate comprising a plurality of sample wells.

13. The system of claim 10, wherein the instructions for pure dye normalization executable by the processor comprise instructions designed to generate a test spectra matrix M.

14. The system of claim 13, wherein matrix Mref and matrix M comprise normalized and averaged spectra.

15. The system of claim 13, wherein the instructions for pure dye normalization executable by the processor further comprise instructions designed to iteratively adjust matrix M until the difference between matrix M and matrix Mref is minimized.

16. The system of claim 15, wherein the instructions for pure dye normalization executable by the processor further comprise instructions designed to modify matrix M based on correction factors for each filter pair.

* * * * *